(12) United States Patent
Kreisberg et al.

(10) Patent No.: US 6,284,025 B1
(45) Date of Patent: Sep. 4, 2001

(54) PARTICLE MICROTRAP SCREEN

(75) Inventors: Nathan Kreisberg, El Cerrito; Susanne V. Hering, Berkeley, both of CA (US)

(73) Assignee: Aerosol Dynamics, Inc., Berkeley, CA (US)

( * ) Notice: Subject to any disclaimer, the term of this patent is extended or adjusted under 35 U.S.C. 154(b) by 0 days.

(21) Appl. No.: 09/412,441

(22) Filed: Oct. 5, 1999

Related U.S. Application Data

(60) Provisional application No. 60/103,573, filed on Oct. 9, 1998.

(51) Int. Cl.$^7$ .......................... B01D 45/08; B01D 50/00; G01N 1/00
(52) U.S. Cl. ................... 95/267; 95/268; 55/315; 55/424; 55/465; 55/DIG. 14; 96/224; 96/413; 73/28.05
(58) Field of Search ............... 95/267, 268, 272; 55/462, 465, DIG. 14, 315, 424; 96/223, 224, 413; 73/28.04, 28.05, 28.06, 863.22, 863.23

(56) References Cited

U.S. PATENT DOCUMENTS

| | | | |
|---|---|---|---|
| 3,741,001 | * 6/1973 | Fletcher et al. | 73/28.05 |
| 3,949,594 | * 4/1976 | Treaftis et al. | 73/28.04 |
| 4,012,209 | * 3/1977 | McDowell et al. | 55/465 |

OTHER PUBLICATIONS

Kim H.T. et al., "New PM10 Inlet design and Evaluation", Aerosol Science and Technology 29, pp. 350–354, 1998.
Biswas, Pratim and Flagan, Richard C., "The Particle Trap Impactor," J. Aerosol Science, vol. 19, No. 1, pp. 113–121, 1988.
Tsai, Chuen–Jinn and Cheng Yu–Hsiang, "Solid Particle Collection Characteristics on Impaction Surfaces of Different Designs," Aerosol Science and Technology 23, pp. 96–106, 1998.
Fang C.P. et al., "Influence of Cross–Flow on Particle Collection Characteristics of Multi–Nozzle Impactors," J. Aerosol Science, vol. 22, No. 4, pp. 403–415, 1991.
Marple, Virgil A. et al., "A Microorifice Uniform Deposit Impactor (MOUDI): Description, Calibration, and Use," Particle Technology Laboratory, Publication No. 758, Department of Mechanical Engineering, University of Minnesota, Minneapolis, Minnesota, 1990.

* cited by examiner

Primary Examiner—Duane Smith
Assistant Examiner—Robert A. Hopkins
(74) Attorney, Agent, or Firm—James Creighton Wray; Meera P. Narasimhan

(57) ABSTRACT

A particle microtrap screen apparatus has an inlet, a jet orifice screen with multiple microjet orifices, and a microtrap plate having multiple microtraps spaced opposite the multiple microjet orifices for entrapping particles entrained by the jets and then released by the gas, and impacting in the microtraps with the energy imparted by the gas as the gas turns and flows between the jet orifice screen and the microtrap impact plate. Collection efficiencies of greater than 90% of particles, about 2 micrometers or larger in size, are experienced with pressure drops of less than 5 millimeters of water. The pressure drop does not increase upon increased loading with particles. The jet orifices have widths of D, about 0.5 millimeters, with spacing between orifices of about 5D and trap width and depth of about 4D and 2D, respectively, with about 2D spacing between the jet orifice screen and the microtrap plate. Ultraviolet lamps in a plenum on the inlet side of the jet orifice screen illuminate the particle traps through the jet orifices for sterilizing microorganisms within the particle traps. The jet orifices are circular or rectangular orifices.

32 Claims, 10 Drawing Sheets

PARTICLE MICROTRAP SCREEN

This application claims the benefit of U.S. Provisional Application No. 60/103,573, filed Oct. 9, 1998.

This invention was made with Government support under grant number 1R43ES0-7299-01A1 awarded by the National Institute of Environmental Health Science, National Institutes of Health. The Government has certain rights in this invention.

BACKGROUND OF THE INVENTION

Removing airborne particles from living and working environments has traditionally been done by filters that rely on a combination of inertial impaction onto, interception with, and diffusion to the filer media's surfaces. The use of all three mechanisms enables efficient filtration over the widest possible range of particle sizes, but at the cost of large collection areas or large pressure drops. Most bacteria and molds are found in supermicrometer sizes that can be removed by inertia alone.

SUMMARY OF THE INVENTION

The purpose of the invention is to efficiently separate and remove airborne particles larger than a certain inertial or aerodynamic size. Specifically, the invention consists of a staggered array of circular jets stationed above a second array of receiving cups or microtraps. The particle-laden airstream passes through the jets and makes a right angle turn over the microtraps. As a result of the particles' inertia, particles above a well-defined aerodynamic size, the cutoff, are deposited into the collection microtraps situated directly beneath each jet orifice.

Three primary applications are identified for this invention: (1) room air cleaning, (2) biological and non-biological particle sampling, and (3) preprocessing of airstreams for purposes of filter collection of all particles smaller than the microtrap screen cutoff.

Air cleaners based on the principle of inertial impaction offer advantages over current filtration methods when targeting airborne tuberculosis bacilli and other microorganisms in the super-micrometer size range. Specifically, inertial impaction-based devices are more compact, require less energy to operate and allow immediate, localized sterilization of any collected Microorganisms. To process large volumes of air at reasonable pressure drops, a standard fibrous air filter (e.g., HEPA) requires a large active surface area and hence large total volume. Impactors relying on an array of small jets on the order of half a millimeter are inherently more compact even if thousands of jets are needed. Moreover, the absence of significant viscous pressure drop in an impactor relative to a fibrous filter means that a relatively lower pressure drop for the former is possible. A lower pressure drop means less mechanical energy must be expended to move air through the cleaner and therefore less energy will be required as well. Collecting particles on an impaction surface allows for sterilization by direct ultraviolet irradiation, which is not possible with fibrous filters where particles are deposited deep within filter matting.

The microtrap screen affords the bounce-free collection of biological or inert particles that can be subsequently removed by suitable means, for instance elutriation, and analyzed by various standard techniques. The current state of the art in microorganism sampling involves collection either into a liquid solution using an impinger or impaction onto an agar substrate for culturing. Both of these methods are severely limited in the volume of air that can be collected by virtue of the fact that they steadily lose moisture from within the collection systems. An impinger no longer functions when the liquid has been exhausted. Once an agar surface is dry, the collected microorganisms will be destroyed through desiccation. The microtrap screen can effectively collect samples over extended periods of time without desiccation and thereby provide more representative samples.

The current federally approved method for bounce-free removal of particles above 2.5 micrometers for purposes of PM2.5 filter sampling is to use either a WINS impactor or a cyclone. The WINS impactor uses oil to prevent particle bounce so that contaminate-free sampling of organic carbon is not possible. Although cyclones avoid the use of oil or grease adhesives, they are inherently bulky and less suitable for personal exposure sampling. The microtrap screen is compact and does not use any adhesives for particle collection and therefore represents an improvement over current methods of providing PM 2.5 filter samples.

If higher pressure drops are acceptable, as with pump driven flows used in samplers, then lower cutoff sizes are achievable by reducing the jet orifice diameter. For instance, reducing the jet diameter by two while doubling the number of jets would reduce the cutpoint by a similar factor at the same time increasing the pressure drop on the order of a factor of four.

Among the aspects of the invention that are unique are (1) use of traps with very small ("micro") orifices; (2) the use of multiple micro-orifices each with their respective trap; (3) a structure that provides proper alignment of the orifices and traps; (4) an orifice arrangement that does not show interference from neighboring jets, and (5) structures that are easily scale to enable the processing of large volumes of air.

Two basic impactor jet geometries are used. One is an array of circular orifices, and the other is a single rectangular slot. Penetration tests were performed at relatively low flowrates (order 5 lpm) using a small number of circular jets (maximum 64) or a single rectangular jet. Full scale flows use thousands of jets. To create an adequate collection capacity, a variety of particle traps were substituted for the collection surfaces of both impactor designs (an array of circular orifices and a single rectangular slot).

A multi-orifice, circular jet impactor produces an air cleaner that efficiently (>90%) removes particles greater than 2 micrometers. Sixty-four 0.5 mm diameter circular jets chemically etched from thin stainless steel screens for penetration tests performed with liquid (DOS) and solid ($Al_2O_3$) test particles. At a total flow rate of 5.3 lpm, the impactor possesses a measured aerodynamic 50% cutpoint of 1.7 micrometers at a pressure drop of 5 mm water. To prevent particle bounce, individual conical shaped traps of various geometries were placed below each orifice. An optimum trap geometry was obtained which eliminates penetration of bouncy aluminum oxide particles to give 95% efficiency of removal at 2 micrometers.

These and further and other objects and features of the invention are apparent in the disclosure, which includes the above and ongoing written specification, with the drawings.

BRIEF DESCRIPTION OF THE DRAWINGS

FIG. 1 is a flowchart of an experimental setup for testing the size dependent penetration through an impactor.

FIG. 2 is a graph of the ratio of the downstream to upstream concentrations as a function of particle size.

FIGS. 3A, 3B and 3C are an exploded view of a screen test impactor, and plan views of circular and rectangular jet screens.

FIGS. 4A, 4B, 4C and 4D are front views of trap geometries.

DETAILED DESCRIPTION OF THE INVENTION

Figure 1:
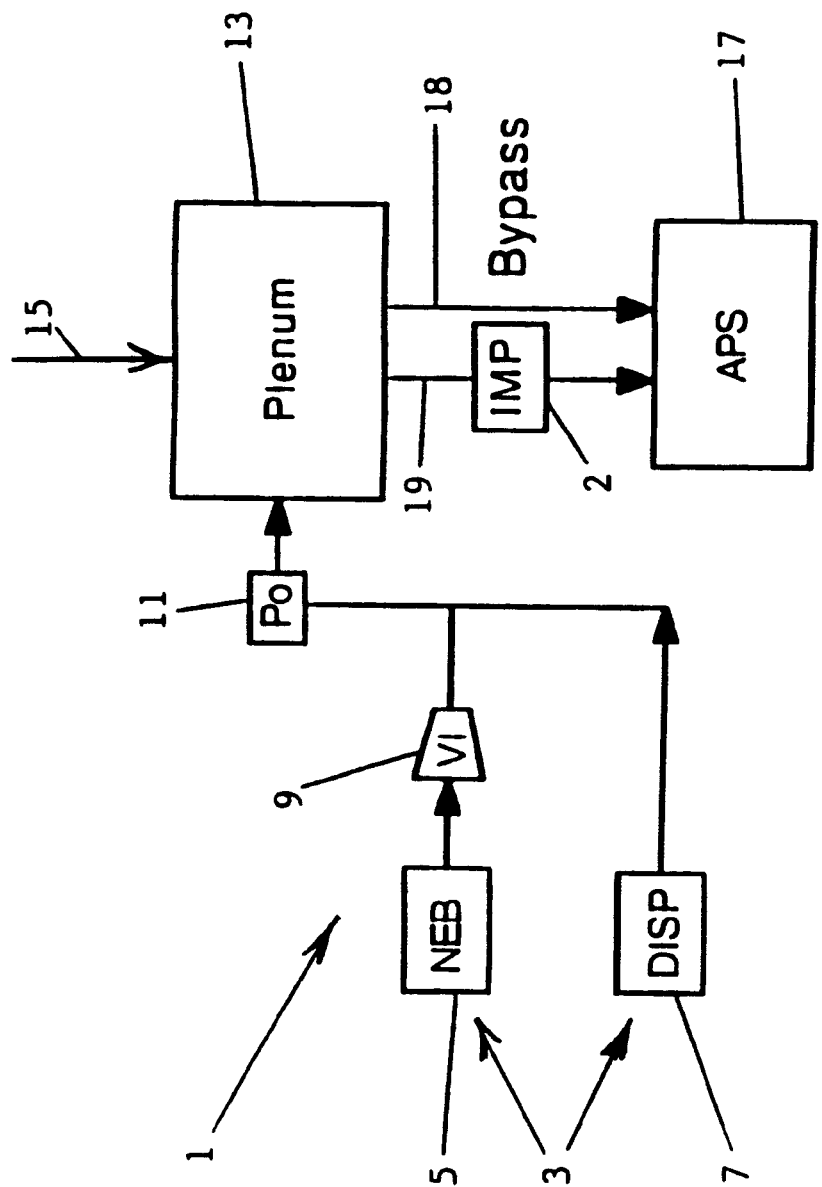

The system 1 used to test impactors 2 is illustrated in FIG. 1 has two aerosol generators 3, a nebulizer 5 for liquid particles (oleic acid), and a dust disperser/elutriator 7 for dry particles ($Al_2O_3$). A virtual impactor 9 reduces the proportion of small particles to large ones from the nebulizer 5. A $Po_{210}$ based neutralizer 11 reduces electrostatic losses. A dilution chamber plenum 13 mixes aerosol streams with dry, filtered air 15. A real time particle counter, the Aerodynamic Particle Sizer 17 measures particle concentrations as a function of particle size. The upstream concentrations are approximated by a bypass line 18 that is identical to the impactor line 19 except the filter holder used to seal the impactor in-line is left empty.

Figure 2:
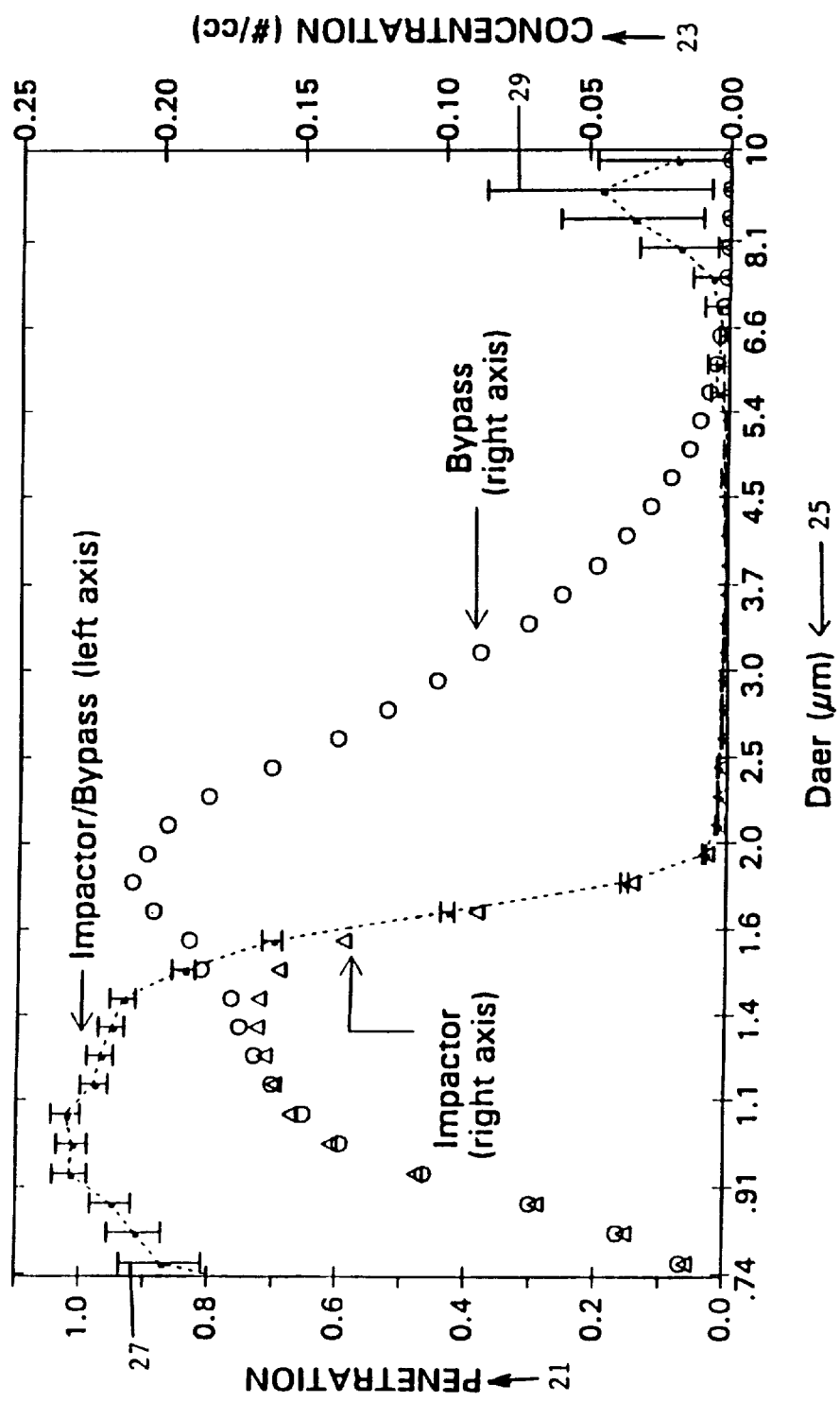

The ratio of the downstream to upstream concentrations as a function of particle size defines a penetration curve (see FIG. 2). Solid aluminum oxide ($Al_2O_3$) aerosols are used to test the effectiveness of particle trap designs in reducing penetration resulting from bouncing particles.

FIG. 2 shows penetration 21 and concentration 23 in relation to aerosol particle diameters 25 in $\mu$m. Particle concentrations above (upstream) and below (downstream) test impactor, and corresponding size-dependent penetration for solid particles impacting on a greased surface. For example shown, impactor has an array of sixty-four (64) 0.05 cm circular jets. Error bars 27 and 29 represent ± 1 standard deviation according to Poisson statistics.

Figure 3A:
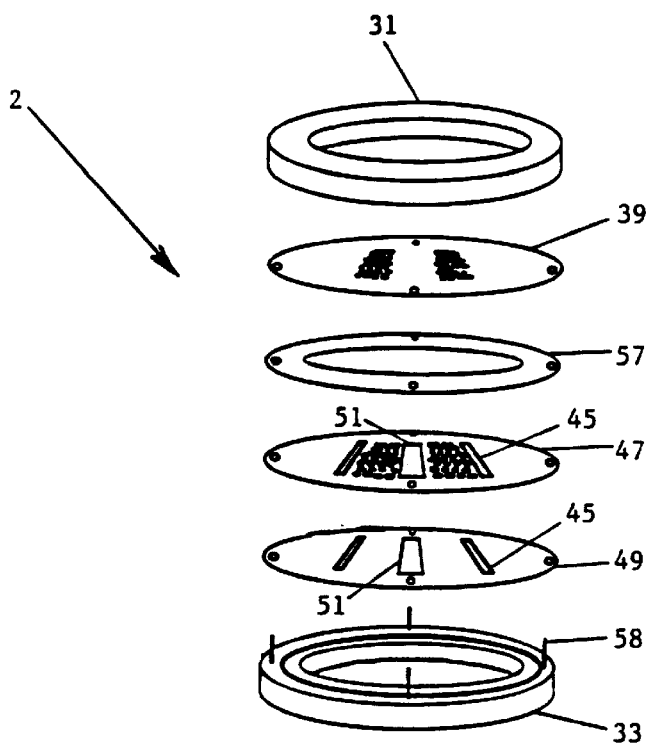
Figure 3B:
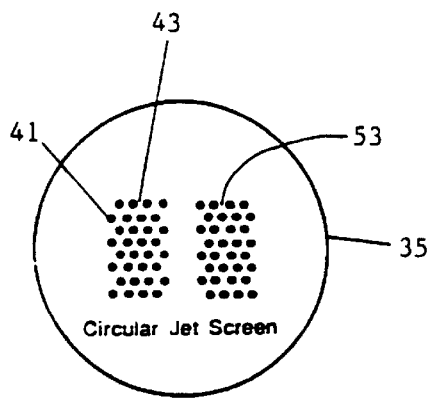
Figure 3C:
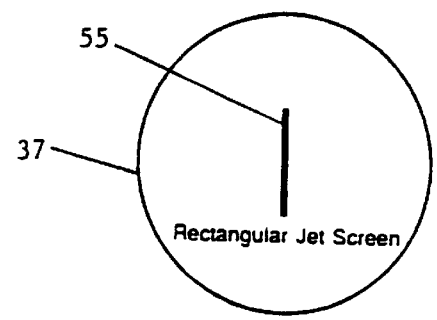
Figure 4B:
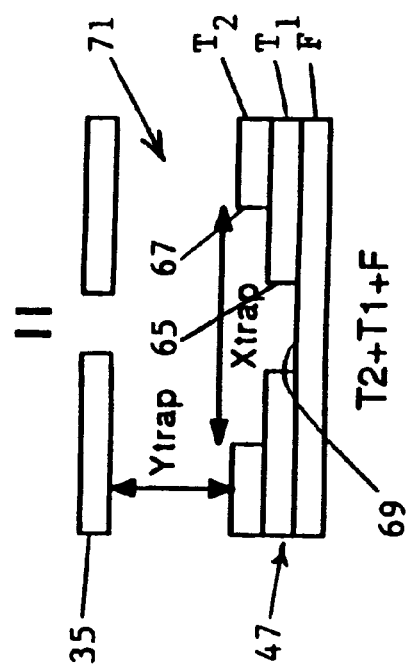
Figure 4A:
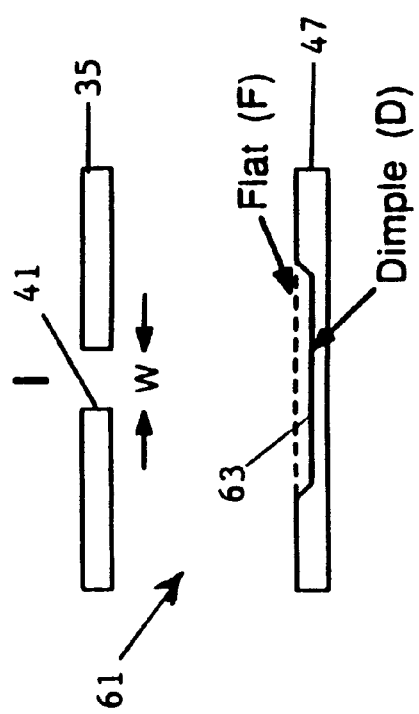
Figure 4D:
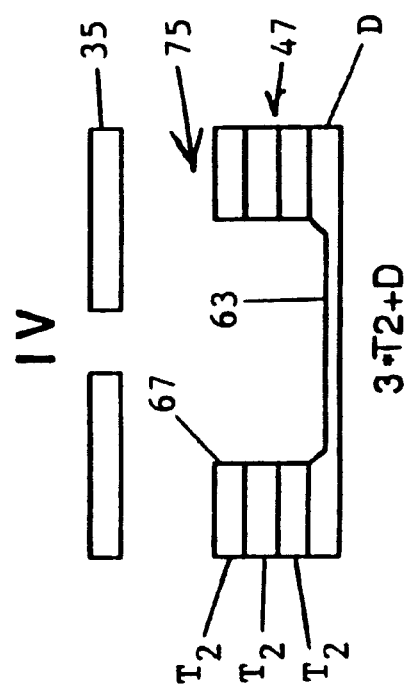
Figure 4C:
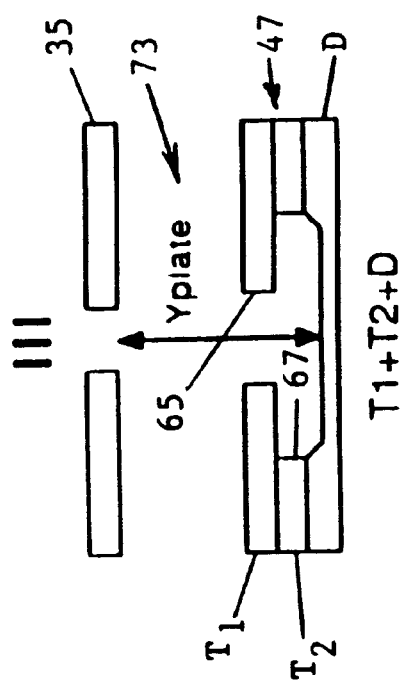

As shown in FIGS. 3A, 3B and 3C, in developing large arrays of jets while avoiding excessive machining costs, orifices chemically etched out of thin stainless steel sheet were used. For initial experiments on circular jets, an off-the-shelf sample of etched sheet was used with a hexagonal pattern of 0.51 mm diameter holes (W) with hole-to-hole spacing of 1.0 mm (2W). Tape was applied to the top of the jet screen leaving arrangements of holes open for use as impactor jets. Impaction plates were situated below the jets and differing gauge wires placed inside o-rings were used to control the spacing and seal, respectively, between the jet and impaction plates. In addition to the jet-to-plate distance, the effect of hole density was investigated by covering strips of holes with different widths of tape.

Once these initial experiments were concluded, impactors 2 were constructed using upper and lower support rings 31 and 33. Circular 35 and rectangular 37 screens were chemically etched to order. All screens were etched from 0.25 mm thick sheets of 316 stainless steel. The circular jets 41 with $W_c$=0.5 mm (FIGS. 3A and 3B) are arranged in two hexagonal-patterned strips 43. The circular jets 41 are arranged in two sections to avoid interference between the jets. Exit slots of width $4W_c$, are placed in the trap screen 47 and impaction plate screen 49 to either side. The center exit slots are joined to make a single slot 51 of double width. The jet-to-jet spacing 53 is $5W_c$. The single rectangular jet 55 (FIG. 3C) with dimensions $W_r$=0.4 mm and L=13 mm has comparable exit slots of $3W_f$ in the trap and plate 49. Both screen geometries include designs with oversized orifices centered over the corresponding jet orifices which form basic elements in the construction of trap walls. By combining different combinations of trap screens with jet 39, spacer 57, trap 47, and impaction 49 screens, stacked together and aligned by registration pins 58 in registration holes 59, a wide variety of impactor geometries are possible, as indicated in FIGS. 4A, 4B, 4C and 4D. A modification of the etching process allows for single side etching, such that a depression or 'dimple' in one face of the screen is possible. This process was used to create impaction plates with dimples equal to four jet diameters on one side and flat surfaces on the other.

Specific examples of traps, shown in FIGS. 4A, 4B, 4C and 4D, applicable to both circular and rectangular jets, illustrate the four fundamental trap geometries tested. The simplest trap 61, type I, consists of a small depression (dimple) 63 half the screen thickness or W/4 in depth and 4W wide. The rest of the trap types involve different combinations of two types of screens, T1 and T2, which possess the same geometry as the respective jet screen except that the apertures are either 2W or 4W wide and additionally possess exit slots 45 and 51 (shown in FIG. 3A). Thus, type II (FIG. 4B) 71 encompasses all open openings, and type III has enclosed openings, while type IV refers to the intermediate case of straight walls of varying depth. Flat 69 or dimpled 63 impaction surfaces may be used with trap designs II through IV.

Efficiency depends on pressure drop and jet density. A first set of experiments was conducted on circular jets 41 (shown in FIGS. 3A and 3B) to explore the dependence of impaction efficiency as measured by the particle diameter corresponding to 50% penetration, $D_{50}$, on the pressure drop across the impactor. Additionally, the effect of orifice density on $D_{50}$ was examined to judge the degree to which jet crowding and the resulting cross-flow leads to impaired performance.

Figure 5:
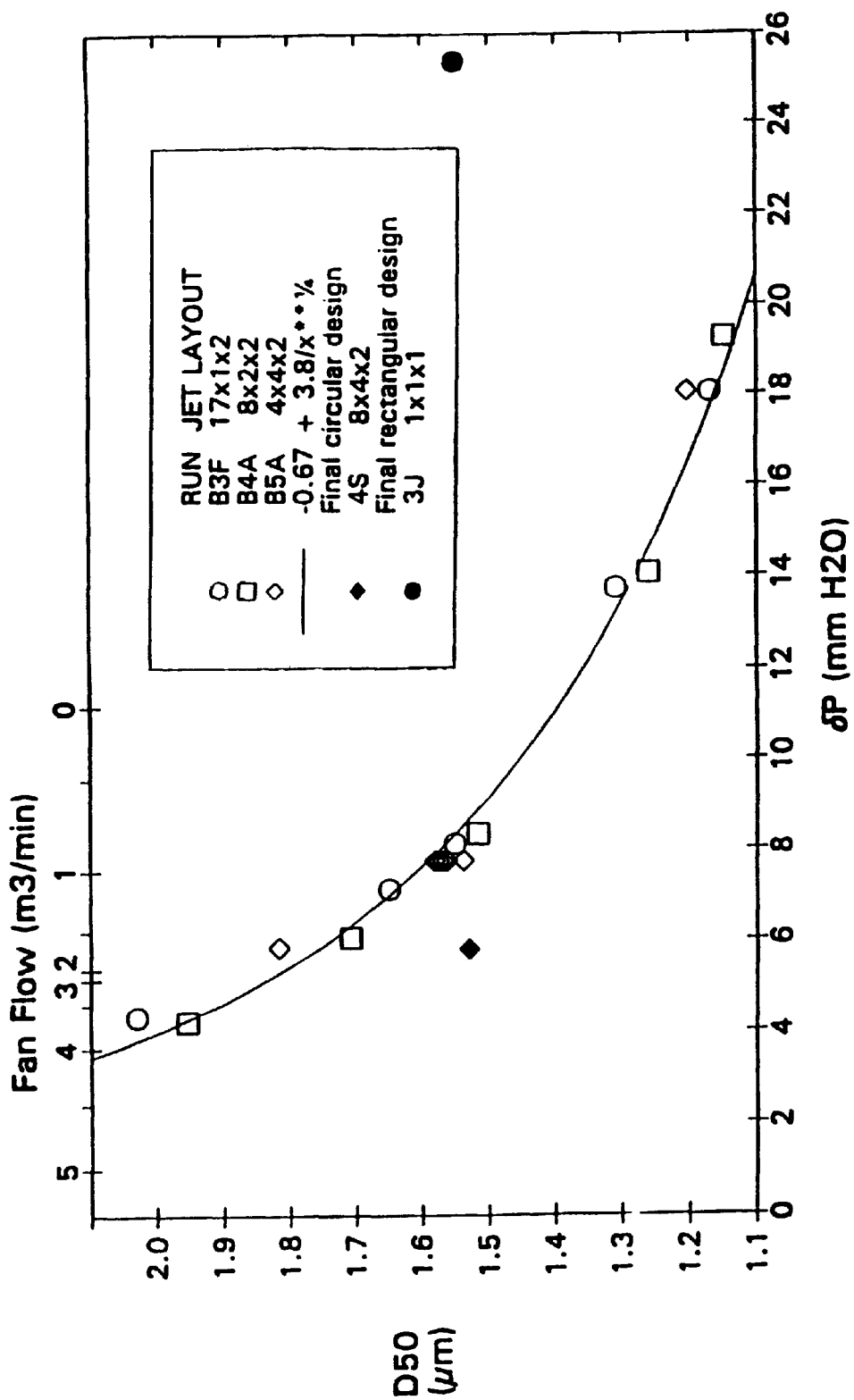
FIG. 5 is a graph of $D_{50}$ versus the resulting pressure drop for several different impactor geometries.
Figure 6:
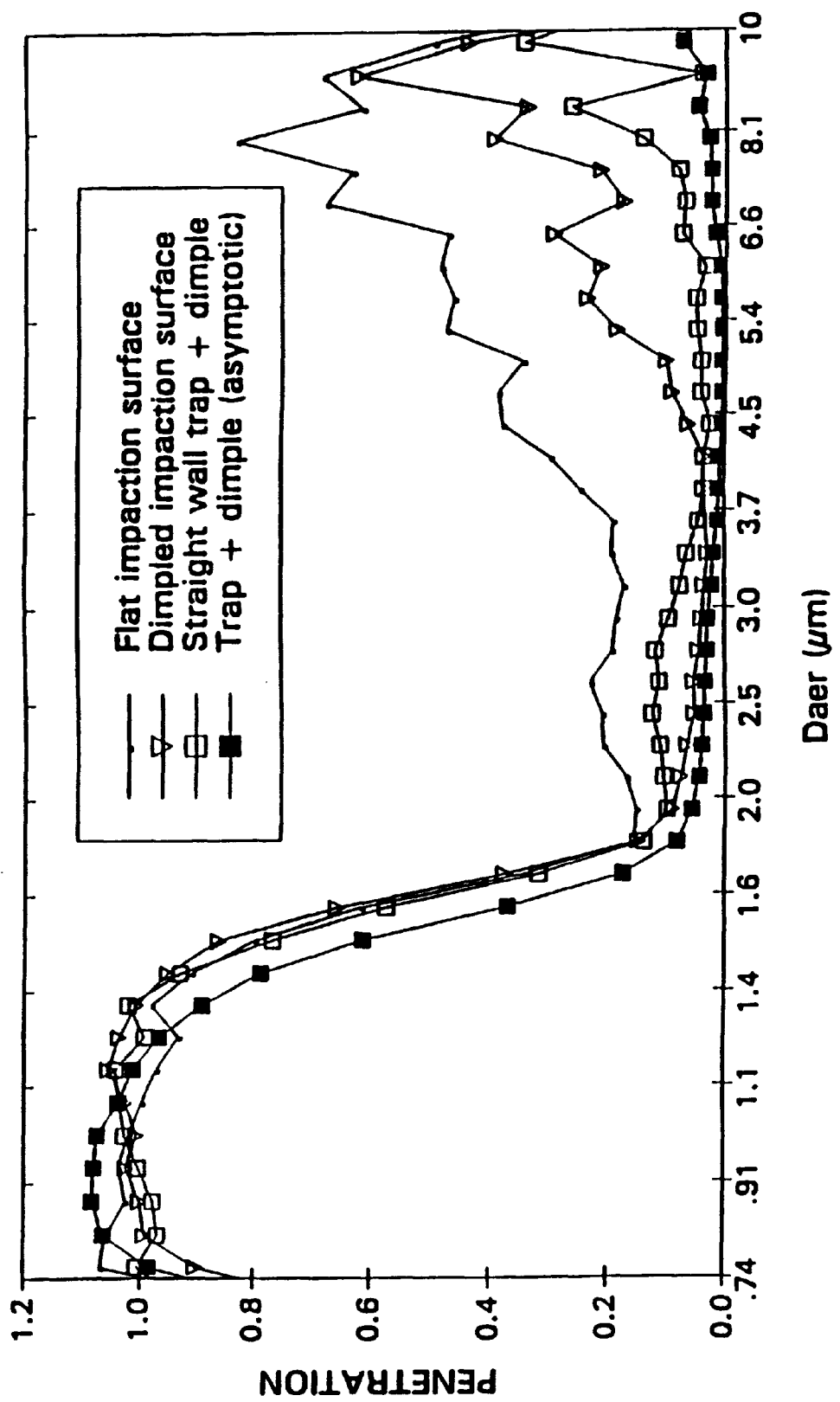
FIG. 6 shows penetration curves for various trap geometries.
Figure 7:
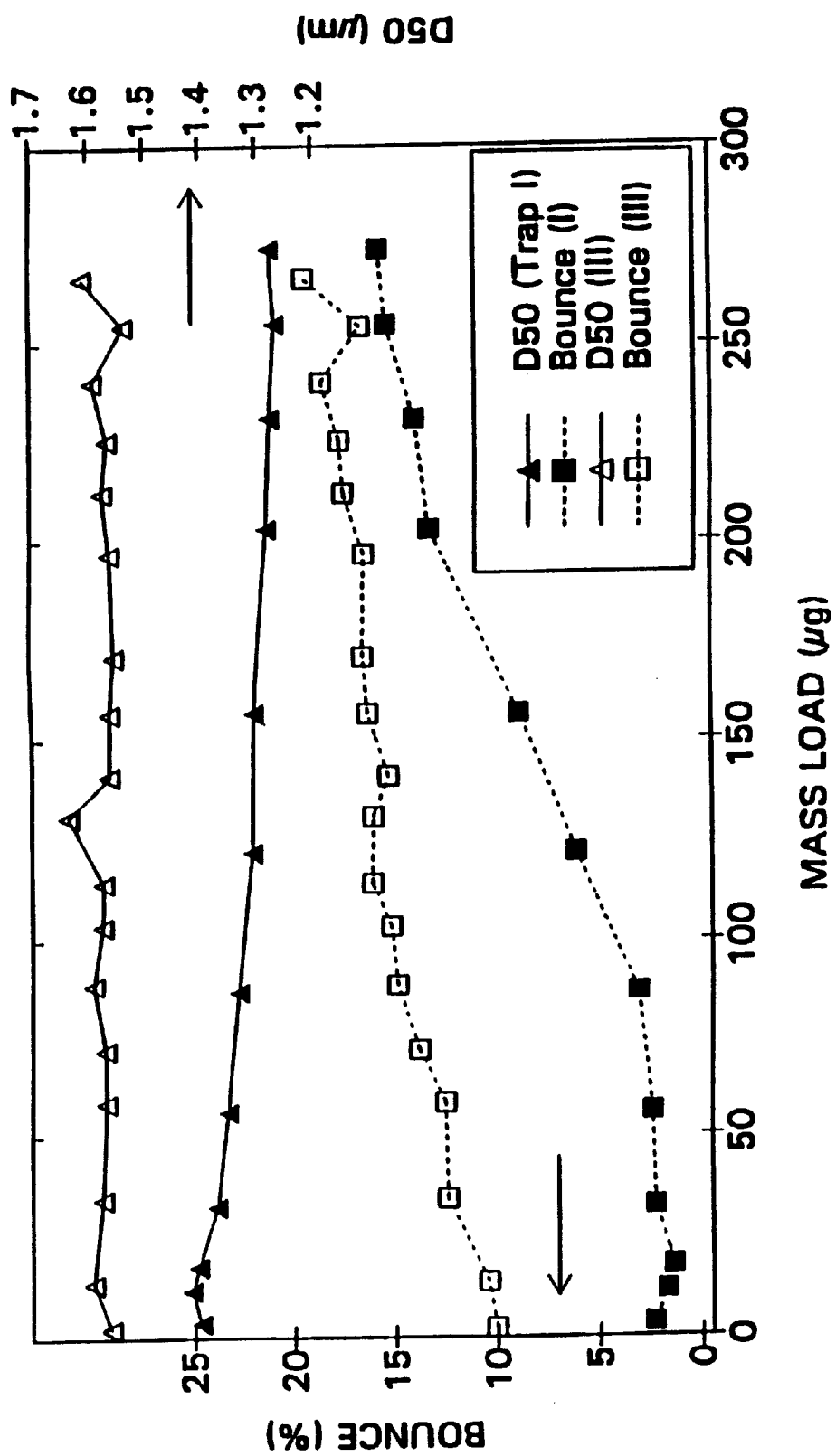
FIG. 7 is a graph of particle bounce and cutpoint versus particle loading on a singular rectangular jet.
Figure 8:
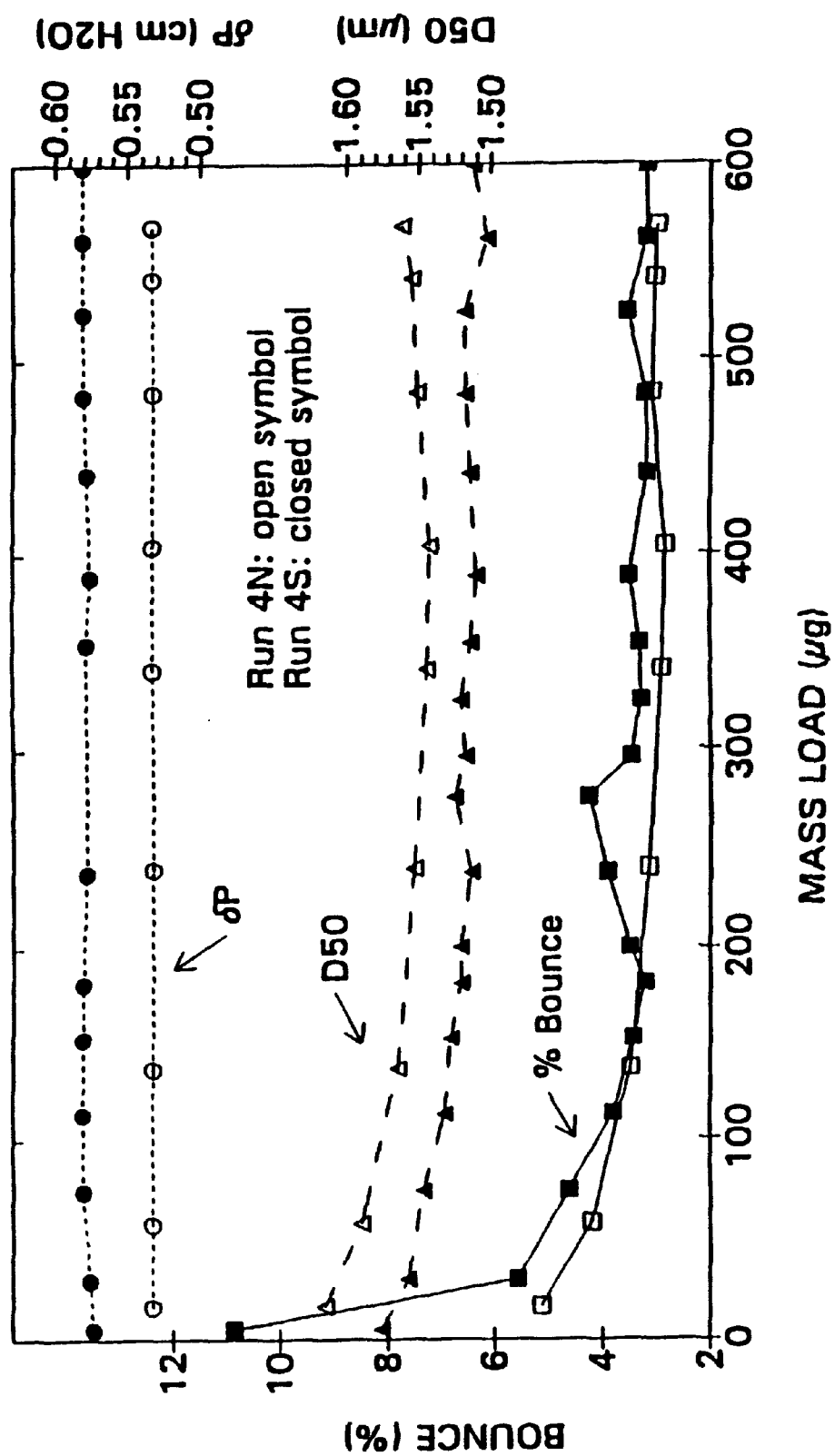
FIG. 8 is a graph of bounce, cutpoint and pressure drop versus particle loading on an optimum circular jet array.
Figure 9:
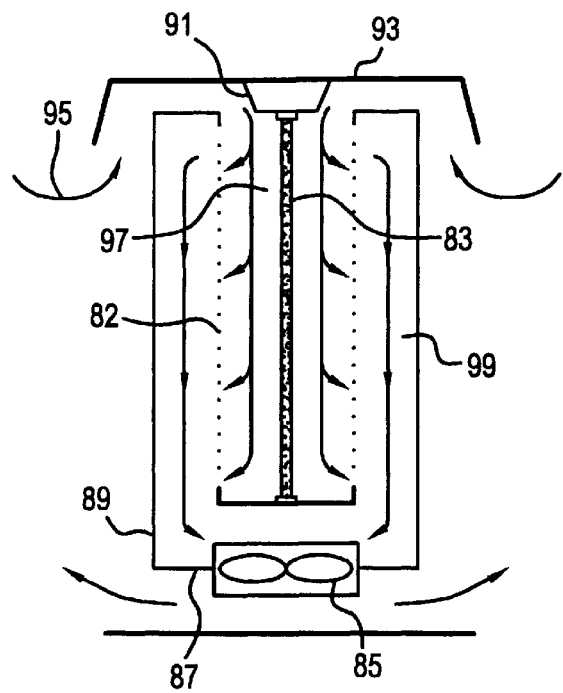
FIG. 9 is a front view of a table/floor air cleaner.
Figure 10:
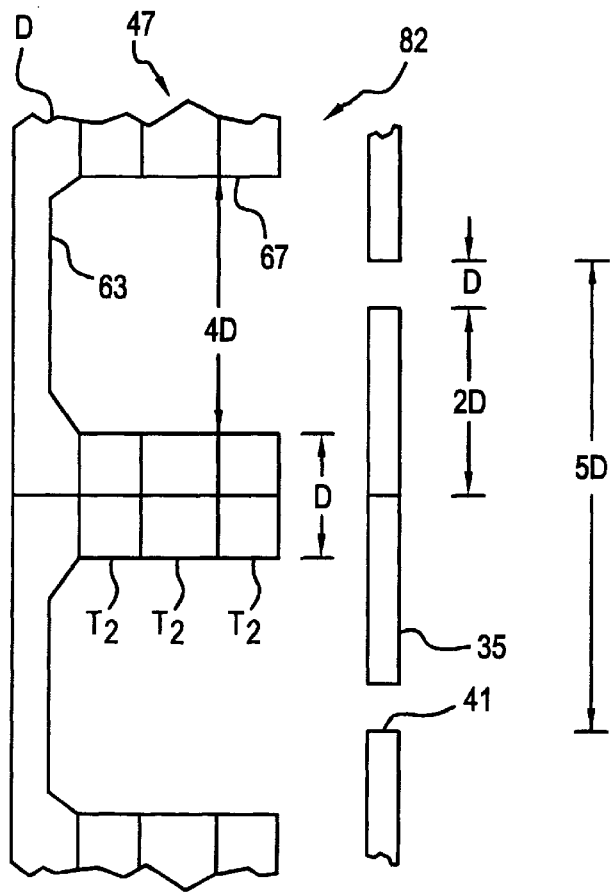
FIG. 10 is a front view of the impactor.

In FIG. 5, particle diameter collected with 50% collection efficiency, $D_{50}$, is plotted against pressure drop, $\delta P$, for varying impactor geometries. Open symbols are arrays of jets with half the jet spacing as that of run 4S accounting for the shift in $D_{50}$ from a common power law (fit line). A single rectangular slot has a significantly higher pressure drop for comparable $D_{50}$. Top ordinate axis shows flow rate for a 16×16 $cm^2$ axial fan at the given $\delta P$.

FIG. 5 shows $D_{50}$ versus the resulting pressure drop, $\delta P$, for several different impactor geometries. Hole layouts are described by the nomenclature R×C×S, representing R rows by C columns in S groupings where the straight columns are aligned with the outflow slots (see FIG. 3A) and the rows are alternately staggered in accordance with the underlying hexagonal pattern. Thus, the final designs (8×4×2, 4S, circular) and (1×1×1, 3J, rectangular) in the legend correspond to FIGS. 3B and 3C, respectively. Open symbols refer to geometries with closely spaced circular jets (2W) that illustrate the relative insensitivity of impactor performance to cross-flow effects. Little difference was observed between one column (circles) and four columns (diamonds) of jets. A common power law of the form $D_{50}=a+b\delta P^{-\frac{1}{4}}$, which has the expected dependence on pressure drop, models all of the open symbol points within the data's scatter. The final design incorporates wider spacing (5W) for the circular jet arrays to accommodate the widest trap openings. The difference between runs 4S and the B series is attributable to this increased jet to jet spacing which allows for more efficient deposition between jets.

Experiments on particle bounce and impactor trap designs conducted on the custom etched screens are summarized in Table 1. Numerous trap geometries were tested for both circular and rectangular jet based impactors as indicated in columns C3, C4 and C6–C8. Impaction surfaces were sometimes initially coated with Vaseline (C5), but loading experiments in which complete layers of aerosol particles are collected indicate that the asymptotic state of impactor efficiency is independent of this preparation. Each run consists of multiple size distribution measurements, alternating between the upstream and downstream lines. Reported for each penetration curve are the final pressure drop (C9), first, last and average $D_{50}$ (C10–12, respectively) and first, last and average penetrating mass fraction above $D_{50}$ (C13–15, respectively). The average mass median aerodynamic diameter (C16) and the total accumulated mass loading on the screen (C17) were determined from the upstream and downstream distributions for each run.

The first set of experiments summarized in Table 1 are for a single rectangular slot. Interpretation of these results is complicated by the undesirable presence of a sonic resonance present to differing degrees with all of the rectangular slot cases. By taping off one of the two exit slots, the generated tone could be reduced but not eliminated. The source of the tone is not known but flexing of the thin screen at an audible frequency is the most likely explanation. Whether or not the presence of more slots (jets and exits) would change this effect is unknown. Ultimately, a thicker screen may be used to increase the stiffness and thereby eliminate this tendency to oscillate. However, the significantly higher pressure drop (~25 mm of water) for a comparable $D_{50}$ relative to the circular jet design, which may in part be due to this unanticipated resonance effect, makes this design less attractive than the round jet design. Various particle traps were tried with one open exit slot but the lowest mass fraction of bouncing particles was achieved with trap type III. Runs 3H–3J were most effective at collecting solid particles (aluminum oxide) with approximately 15% of the mass above the cutpoint diameter penetrating the impactor.

The second set of experiments summarized in Table 1 cover the circular jet designs. As compared to the rectangular slot case, the round jets produce a comparable cutpoint at one fifth the pressure drop. FIG. 6 shows representative penetration curves for different trap geometries illustrating the effectiveness of particle traps in preventing particles from bouncing off initially cleaned impaction surfaces (points and open symbols). The greatest amount of particle bounce is observed with a flat impaction surface (points) while the simple addition of the dimpled impaction plate (triangles, trap I, FIG. 4A) greatly reduces the penetration above the cutpoint. Alternatively, the initial response of a clean trap consisting of straight walls (squares, trap IV, FIG. 4D) possesses greater bounce in the 2–4 μm and less above 4 μm than type I. After sufficient loading, however, the performance of the straight walled trap (filled squares) is far superior to any other geometry tested. For this case, $D_{50}$=1.6 μm with the penetration at 2 μm of about 5% at a pressure drop of only 5 mm of water.

FIG. 7 shows the effect of particle loading on impactor performance as a result of a loading experiment on a single rectangular jet with a trap (type III, FIG. 4C) and with no trap (type I with dimple). The graph shows percent of mass above the cutpoint which penetrates the impactor. Ideally, this fraction is zero. In practice, penetration above $D_{50}$ is finite, primarily because of particle rebound from the impaction surface. Hence, the use of the shorthand 'Bounce' in FIGS. 7 and 8. To a limited extent, non-ideal impactor cut-off may result from deviations from ideal impactor flow patterns as may be induced by the presence of particle traps.

For this experiment the impaction surfaces were initially greased with Vaseline. Penetration increases with loading as particles progressively cover the greased surface causing subsequent particles to rebound from those previously deposited. The presence of a trap initially degrades the performance of the impactor with respect to penetration but after sufficient loading this geometry approaches the performance of the non-trap case but with a consistently higher cutpoint. The cutpoint is not observed to change for the trap case, but it decreases slightly for the non-trap case. The pressure drop for both cases is 25 mm of water.

FIG. 8 shows results of two loading experiments on the optimum circular jet array with a straight well trap (IV) of depth 1.5W. These runs, conducted on different occasions (4N and 4S) with initially ultrasonically cleaned impaction surfaces, illustrate a rapid approach to an asymptotic state with bounce fraction below 4%. Run 4N corresponds to squares in FIG. 6 (open squares, ~6 μg; filled squares, >200 μg). Note that the pressure drop, δP, and to a lesser extent the cutpoint, $D_{50}$, are unaffected by loading. This insensitivity of pressure drop to loading is in sharp contrast to traditional air filters where the build up of collected dust invariably leads to a reduction in flow capacity. The difference in δP and $D_{50}$ between the two runs may be accounted for by differences in flow rate of only 5%.

The total collection capacity of this trap design is quite large. The volume of each trap is approximately 3 μl, so that if an input concentration of 50 μg/m$^3$ were assumed, which is conservatively high for indoor air, then the time to fill just half of each trap would be on the order of three years. Therefore, at this assumed loading rate, if the trap were cleaned once a year, only 15% of the air cleaner's total collection capacity would be reached.

Integral to the use of an impactor as a means of removing supermicrometer particles is the desire to permit direct irradiation of collected organisms for sterilization. Since the gap between the jet screen and the trap/impaction assembly for the best case described above is on the order of 1 mm, introducing UV illumination from within this space is virtually impossible. Rather, the open nature of the trap entrance situated below the jet opening suggests that irradiation of the impaction surface through the jet orifice may be sufficient to irradiate any particles collected.

Using etched aluminum for the screen material provides a high degree (>85%) of reflectance from the jet screen surface. If the etched screen were bent into a cylinder surrounding the UV tube lamp, then the light incident on the jet opening may be approximated by an isotropic source because of internal reflections. For the trap type IV geometry that gave a minimum penetration (Runs 4K–4S and 4N of Table 1), where the gap between jet and trap screens is 1.5W and the trap entrance is 4W, a simple calculation shows that as long as the jet screen thickness is equal to or less than the jet diameter, incoming light from the orifice will directly illuminate all of the interior surfaces of the trap.

In one embodiment, illustrated in FIG. 9, air cleaner 81 incorporates the jet and impaction screen impactor 82 (shown in FIG. 10) as a continuous cylindrical tube with the lamp 83 running down the center axis. Fan 85 is at one end 87 of the tube assembly housing 89. The lamp fixture 91 is placed at the opposite end 93. Air 95 to be processed enters at one end 93 of the housing 87, flows into the central cavity 97, flows around the lamp 83, and passes through the jets of impactor 82 in an outward radial path, flows down an annular passage 99 outside the jet, trap, and impactor screens in impactor 82, and passes through the fan 85 and out the other end 87 of the air cleaner unit 81. This commercial air cleaner makes optimum use of the inherent geometry of the lamp and axial fan to produce a highly compact device. Alternative designs provide for installation on ceilings or in ventilation ducts.

Axial fans are suitable for an impactor-based air cleaner. To minimize noise produced by an impactor-based air cleaner, an axial fan is ideally used for the air mover. A fan's capacity to deliver flow is dependent on the flow impedance (i.e. pressure drop) presented to it. The performance of a specific axial fan (Nidec model TA600DC) taken from the manufacturers literature is indicated by the top scale on the ordinate axis of FIG. 5, which shows the flow rate for a 16×16 cm$^2$ axial fan at the given δP. Using such a fan in a scaled-up device may filter up to 1.5 m$^3$/min requiring 19,200 orifices. Similar fans exist which could handle greater δP's (i.e. D$_{50}$) or, conversely, greater flow rates at the same pressure drop.

Penetration measurements of various jet and particle trap designs show that air cleaning devices and biological specimen collectors based on inertial impaction may be highly efficient at removing super-micrometer particles, including those posing particular risks, such as biological hazards and allergens, and those that have the tendency to bounce.

Two impactor-based approaches use circular orifices and rectangular slots. Slotted jets offer the advantage of compatibility with particle traps. Circular jets, however, perform better than slots (i.e. lower cutpoint for a given δP) and are compatible with individual traps as well. Of these two approaches, impactors with circular jets and traps was shown to be superior and to have met all of the desired criterion.

Circular and rectangular jet designs with customized traps possess collection efficiencies greater than 90% for particles ≧2 μm in size. Pressure drops within the capacity of axial fans are obtained (5 mm of water).

Open cavity particle traps possess large capacities for collected particles. An annual maintenance schedule may be achieved.

The new impactors have a particle trap geometry that is suitable for direct UV exposure.

Impactor-based air cleaning devices provide real advantages over conventional filtration methods for the selective removal and sterilization of airborne micro-organisms such as tuberculosis bacilli. The introduction of a successful collection technology, termed the particle microtrap screen, as represented by the circular traps described herein provide impactor-based devices and highly compact, energy efficient, low maintenance air cleaners and biological particle samplers.

The invention provides a multi-jet impactor to efficiently remove particles above 2 micrometers and to reduce particles below 2 micrometers. The invention provides collection >95% for particle sizes ≧2 μm and >50% reduction for particles ≧1.5 μm at a pressure drop of 5 mm water. The new micro-orifice particle traps essentially eliminate solid particle bounce and provide large loading capacities, without impairment of impactor performance. The invention provides efficient air filtration devices targeting supermicrometer particles posing particular risks (e.g., bacteria and allergens). If one were primarily interested in only removing particles above a specified size then inertial impaction alone is sufficient. Indeed, an air cleaner based solely on inertial impaction potentially offers several advantages over traditional filtration including lower energy costs because of lower pressure drops and constant performance independent of loading. An example of a desirable target class of particles is that of airborne bacteria which are 1–5 micrometers in aerodynamic diameter when in droplet form.

While the invention has been described with reference to specific embodiments, modifications and variations of the invention may be constructed without departing from the scope of the invention.

TABLE 1

Summary of screen impactor experiments with optimum trap configurations shaded.

| Run ID[1] | Aerosol[2] | Trap Type[3] | Trap Geometry[4] | Initial Coating[5] | $X_{trap}$/W[6] | $Y_{trap}$/W[7] | $Y_{plate}$/W[8] | ΔP cm $H_2O$[9] | $D_{50}$ First, μm[10] | $D_{50}$ Last, μm[11] | $D_{50}$ Avg, μm[12] | Bounce First, %[13] | Bounce Last, %[14] | Bounce Avg., %[15] | MMAD Load, μm[16] | $M_{accum}$ Load, μg[17] | Cont.[18] |
|---|---|---|---|---|---|---|---|---|---|---|---|---|---|---|---|---|---|
| Single Rectangular Jet; 2 exit slots | | | | | | | | | | | | | | | | | |
| 1A | OA | NT | F | None | | | 3 | 1.57 | 1.90 | 1.90 | 1.90 | 3.4 | 2.8 | 3.3 | 3.97 | 4.8 | |
| 2A | OA | NT | F | None | | | 3 | 2.30 | 1.55 | 1.54 | 1.55 | 9.3 | 1.54 | 7.3 | 3.19 | 3.1 | |
| 2B | OA | NT | F | None | | | 5 | 2.26 | 8.71 | | 3.71 | 36.7 | | 36.7 | 4.92 | 0.0 | |
| 2C | OA | NT | F | None | | | 4 | 2.29 | 1.56 | | 1.56 | 6.2 | | 6.2 | 3.34 | 1.6 | |
| 2D | OA | NT | F | None | | | 5 | 2.29 | 1.53 | | 1.53 | 7.6 | | 7.6 | 3.45 | 3.0 | |
| Single Rectangular Jet: 1 exit slot | | | | | | | | | | | | | | | | | |
| 2E | $Al_2O_2$ | NT | F | None | | | 3 | 2.44 | 1.43 | 1.43 | 1.43 | 36.9 | 42.5 | 39.7 | 3.84 | 5.3 | |
| 2G | $Al_2O_3$ | NT | F | Vaseline | | | 3 | 2.37 | 1.40 | 1.41 | 1.41 | 2.3 | 1.4 | 1.8 | 3.61 | 17.5 | |
| 2H | $Al_2O_3$ | NT | F | Vaseline | | | 3 | 2.40 | 1.37 | 1.28 | 1.31 | 2.3 | 15.7 | 9.0 | 3.49 | 274.0 | |
| 3A | $Al_2O_3$ | I | D | None | | | 3.25 | 2.44 | 1.30 | 1.29 | 1.29 | 38.5 | 39.4 | 39.5 | 3.45 | 5.6 | |
| 3B | $Al_2O_3$ | II | T1 + T2 + D | Aerosol | 2 | 2 | 3.25 | 2.59 | 1.68 | 1.74 | 1.71 | 19.3 | 20.8 | 20.1 | 3.64 | 7.2 | x |
| 3C | $Al_2O_3$ | II | T1 + T2 + D | None | 2 | 2 | 3.25 | 2.64 | 1.60 | | 1.60 | 26.7 | | 26.7 | 3.65 | 1.1 | |
| 3D | $Al_2O_3$ | II | T1 + T2 + D | Aerosol | 2 | 3 | 4.25 | 2.54 | 1.77 | 1.78 | 1.78 | 31.6 | 32.8 | 32.2 | 3.64 | 5.8 | x |
| 3E | $Al_2O_3$ | IV | 2* T2 + D | Aerosol | 4 | 2 | 3.25 | 2.77 | 1.40 | 1.40 | 1.40 | 29.7 | 32.4 | 30.7 | 3.58 | 13.0 | x |
| 3F | $AlO_x$ | IV | T2 + D | Aerosol | 4 | 2.5 | 3.25 | 2.67 | 1.41 | 1.41 | 1.41 | 31.8 | 31.3 | 31.5 | 3.61 | 16.8 | x |
| 3G | $Al_2O_3$ | IV | T2 + D | None | 4 | 2.5 | 3.25 | 2.67 | 1.42 | 1.42 | 1.42 | 22.6 | 24.0 | 24.0 | 2.94 | 11.8 | |
| 3H | $Al_2O_3$ | III | T1 + T2 + D | Vaseline | 2 | 2 | 3.25 | 2.54 | 1.56 | 1.64 | 1.58 | 10.0 | 16.1 | 13.5 | 3.22 | 130.9 | |
| 3I | $Al_2O_3$ | III | T1 + T2 + D | Vas./Aer. | 2 | 2 | 3.25 | 2.54 | 1.56 | 1.38 | 1.52 | 15.3 | 12.9 | 15.3 | 2.94 | 185.0 | x |
| 3J | $Al_2O_3$ | III | T1 + T2 + D | Vas./Aer. | 2 | 2 | 3.25 | 2.54 | 1.56 | 1.41 | 1.55 | 16.4 | 13.9 | 17.2 | 3.61 | 286.7 | x |
| Multiple Circular Jets: two hexagonal patterns of 32 jets each, 3 exit slots total | | | | | | | | | | | | | | | | | |
| 4A | $Al_2O_3$ | NT | F | Vaseline | | | 3 | 0.56 | 1.71 | | 1.71 | 9.0 | | 9.0 | 3.21 | 2.8 | |
| 4B | $Al_2O_3$ | I | D | Vaseline | | | 3.25 | 0.53 | 1.70 | 1.69 | 1.69 | 2.9 | 2.9 | 2.9 | 3.30 | 4.3 | |
| 4C | $Al_2O_3$ | I | D | Vaseline | | | 6.25 | 0.53 | 1.87 | 1.86 | 1.87 | 2.9 | 2.8 | 2.8 | 3.39 | 4.2 | |
| 4D | $Al_2O_3$ | NT | F | None | | | 3 | 0.56 | 1.67 | 1.65 | 1.66 | 36.0 | 29.0 | 32.5 | 3.13 | 2.8 | |
| 4E | $Al_2O_3$ | I | D | None | | | 3.25 | 0.53 | 1.67 | 1.67 | 1.67 | 18.1 | 10.0 | 13.9 | 3.17 | 6.6 | |
| 4F | $Al_2O_3$ | IV | T1 + D | None | 2 | 3 | 3.25 | 0.51 | 1.66 | | 1.66 | 9.3 | | 9.3 | 3.29 | 2.3 | |
| 4G | $Al_2O_3$ | II | T1 + T2 + D | None | 2 | 2.5 | 3.75 | 0.48 | 1.95 | 1.91 | 1.93 | 42.0 | 33.0 | 37.5 | 3.25 | 2.7 | |
| 4H | $Al_2O_3$ | III | T2 + T1 + D | Aerosol | 4 | 2 | 3.25 | 0.50 | 2.10 | 2.08 | 2.09 | 36.5 | 31.7 | 34.1 | 3.46 | 7.1 | |
| 4I | $Al_2O_3$ | II | TI + 2*T2 + D | None | 2 | 2 | 3.25 | 0.50 | 1.92 | 1.91 | 1.91 | 33.3 | 25.5 | 29.4 | 3.38 | 2.9 | |
| 4J | $Al_2O_3$ | II | TI + 2*T2 + D | None | 2 | 1.5 | 3.25 | 0.54 | 2.22 | 2.16 | 2.19 | 32.3 | 18.5 | 26.5 | 3.61 | 16.5 | |
| 4K | $Al_2O_3$ | IV | 3*T2 + D | None | 4 | 1.5 | 3.25 | 0.53 | 1.69 | 1.68 | 1.68 | 15.9 | 14.5 | 15.2 | 3.58 | 2.4 | |
| 4L | $Al_2O_3$ | IV | 3*T2 + D | None | 4 | 1.5 | 3.25 | 0.55 | 1.65 | 1.64 | 1.64 | 9.5 | 7.9 | 8.7 | 3.50 | 6.0 | |
| 4M | $Al_2O_3$ | IV | 3*T2 + D | Aerosol | 4 | 1.5 | 3.25 | 0.56 | 1.60 | 1.61 | 1.60 | 20.1 | 3.7 | 11.9 | 3.01 | 9.9 | |
| 4N | $Al_2O_3$ | IV | 3*T2 + D | None | 4 | 1.5 | 3.25 | 0.53 | 1.61 | 1.56 | 1.56 | 5.1 | 3.0 | 3.4 | 3.52 | 568.0 | |
| 4O | $Al_2O_3$ | III | 3*T2 + T1 + D | None | 4 | 1.5 | 3.75 | 0.58 | 1.85 | 1.82 | 1.84 | 35.6 | 23.0 | 29.3 | 3.48 | 11.8 | |
| 4P | $Al_2O_3$ | IV | 3*T2 + D | None | 4 | 2 | 3.75 | 0.57 | 1.61 | 1.60 | 1.61 | 17.7 | 11.5 | 14.6 | 3.65 | 9.4 | |
| 4Q | $Al_2O_3$ | IV | 3*T2 + D | None | 4 | 1 | 2.75 | 0.65 | 1.57 | 1.54 | 1.55 | 16.5 | 6.2 | 10.0 | 3.53 | 24.6 | |
| 4R | $Al_2O_3$ | IV | 3*T2 + D | None | 4 | 2 | 3.25 | 0.57 | 1.59 | 1.57 | 1.51 | 14.3 | 7.9 | 10.7 | 3.59 | 15.1 | |
| 4S | $Al_2O_3$ | IV | 3*T2 + D | None | 4 | 1.5 | 3.25 | 0.58 | 1.58 | 1.51 | 1.53 | 10.9 | 3.2 | 4.1 | 3.58 | 599.0 | |
| 4T | $Al_2O_3$ | IV | 2*T2 + D | None | 4 | 1.5 | 2.75 | 0.59 | 1.58 | 1.53 | 1.55 | 11.7 | 4.0 | 6.6 | 3.72 | 96.6 | |

Heading Definition

TABLE 1-continued

| Summary of screen impactor experiments with optimum trap configurations shaded. | |
|---|---|
| [1]Run ID | Experiment run identifier (chronological order). |
| [2]Aerosol | Type of aerosol used in experiment: OA ≡ oleic acid, $Al_2O$ ≡ aluminum oxide. |
| [3]Trap Type | NT = no trap, I–IV refer to basic trap configurations as illustrated in FIG. 3. |
| [4]Trap Geometry | Composition of trap with combinations of screen elements T1, T2 and F or D. T1, T2 are trap wall elements with openings equal to 2, 4 times the jet width. Impaction surface is (either flat (F) or dimpled (D). See FIG. 2. |
| [5]Initial Coating | Indicates impaction surface preparation prior to run. Coatings are either Vaseline or previously deposited aerosol. |
| [6]$X_{trap}/W$ | Trap opening width in dimensions of jet width, W. |
| [7]$Y_{trap}/W$ | Distance from bottom of jet surface to top of trap opening in dimensions of jet width, W. |
| [8]$Y_{trap}/W$ | Distance from bottom of jet surface to top of impaction surface in dimensions of jet width, W. |
| [9]$\Delta P$ (cm $H_2O$) | Pressure drop measured directly across impactor clement. |
| [10]$D_{50}$ (First, $\mu$m) | Aerodynamic diameter for 50% penetration for first impactor sample taken. |
| [11]$D_{50}$ (Last, $\mu$m) | Aerodynamic diameter for 50% penetration for last impactor sample taken. |
| [12]$D_{50}$ (Avg., $\mu$m) | Arithmetic mean of $D_{50}$ for all impactor samples taken. |
| [13]Bounce (First, %) | Fraction of mass above $D_{50}$ which penetrates for first impactor sample taken. |
| [14]Bounce (Last, %) | Fraction of mass above $D_{50}$ which penetrates for last impactor sample taken. |
| [15]Bounce (Avg., %) | Arithmetic mean of mass bounce fractions for all impactor samples taken. |
| [16]MMAD (Load, $\mu$m) | Arithmetic mean of mass median aerodynamic diameter (MMAD) for collected aerosol. |
| [17]$M_{accum}$ (Load, $\mu$g) | Calculated accumulated mass loading on impactor for last sample. |
| [18]Cont. | 'x ' indicates continuation of loading from preceding run. |

We claim:

1. Apparatus for air cleaning, particle collecting, biological specimen sampling, comprising a jet screen having multiple jet openings, impact and trap assembly having multiple particle traps aligned opposite the multiple jet openings for impacting and trapping particles entrained in the gas through the jet openings, an air inlet connected to the multiple jet screen, and an air outlet in communication with a space between the multiple jet screen and the multiple particle impact and trap assembly for flowing air to the screen and through the multiple jets and impacting and trapping particles entrained by the air in the traps, and for turning and slowing the air for preventing entrainment or reentrainment of the particles, and for flowing the air from which the particles for sampling have been removed to the air outlet.

2. The apparatus of claim 1, wherein the collected particles are in ranges above 1 micrometer in size, wherein the jets are about 0.5 millimeters in transverse dimension and are spaced about 2.5 millimeters apart on the jet screen, and wherein the particle traps are about 2 millimeters in transverse dimension, with a gap between the trap and jet screens of about 1 millimeter.

3. The apparatus of claim 1, wherein the jet orifices are circular.

4. The apparatus of claim 1, wherein the jet orifices and the traps are circular.

5. The apparatus of claim 1, wherein the jet orifices and the traps are rectangular.

6. The apparatus of claim 1, wherein the jet orifices have a transverse dimension of about D and spacing between the orifices has a dimension of about 5D, and wherein the particle traps have a transverse dimension of about 4D.

7. The apparatus of claim 6, wherein the spacing between the jet orifice screen and the particle trap plate is about 2D and the depth of the particle traps is about 2D.

8. The apparatus of claim 1, further comprising an ultraviolet lamp positioned by the jet orifice screen for illuminating the particles traps through the jet orifices and killing microorganisms within the particle traps for localized sterilizing of any collected microorganisms.

9. The apparatus of claim 8, wherein the ultraviolet lamp is in the form of a tube, wherein the jet orifice screen is in the form of a cylinder surrounding the lamp, and wherein the particle impact and trap plate assembly is in the form of a cylinder surrounding the jet orifice screen, and further comprising an enclosure surrounding the particle impact and trap assembly.

10. The apparatus of claim 9, wherein the air inlet comprises an inlet for admitting air between the lamp and the jet orifice screen at one end of the enclosure, and wherein the outlet comprises an axial outlet at an opposite end of the enclosure.

11. The apparatus of claim 10, further comprising a fan connected to the axial outlet for drawing air into the inlet, between the lamp and the jet orifice screen, through the jet orifice screen, along the particle impact and trap assembly, through the enclosure and out through the outlet.

12. The apparatus of claim 1, wherein the jet orifice screen is constructed by etching jet orifices in a thin plate, and wherein the particle traps are made by etching particle trap openings partially through relatively thick plates.

13. A method of cleaning air, collecting particles, sampling biological specimens, comprising admitting air with suspended particles through an inlet, flowing the air through multiple jet orifices in a jet orifice screen, entraining particles in the air flowing through the jet orifices, impacting particles in multiple particle traps on a particle impact and trap assembly opposite the jet orifice screen, and flowing air from which particles for sampling have been removed between the particle impact and trap assembly and the jet orifice screen and through an outlet.

14. The method of claim 13, wherein the trapped particles are in ranges above 1 micrometer in size, wherein the jets are about 0.5 millimeters in transverse dimension and are spaced about 2.5 millimeters apart on the jet screen, and wherein the particle traps are about 2 millimeters in transverse dimension.

15. The method of claim 13, wherein the jet orifices have a transverse dimension of about D and spacing between the orifices has a dimension of about 5D, and wherein the particle traps have a transverse dimension of about 4D, wherein the spacing between the jet orifice screen and the particle trap plate is about 2D and the depth of the particle traps is about 2D.

16. The method of claim 13, further comprising positioning an ultraviolet lamp by the jet orifice screen, illuminating the particles traps through the jet orifices, and killing microorganisms within the particle traps for localized sterilizing of any collected microorganisms.

17. The method of claim 16, wherein the ultraviolet lamp is in the form of a tube, wherein the jet orifice screen is in the form of a cylinder surrounding the lamp, and wherein the particle impact and trap plate assembly is in the form of a cylinder surrounding the jet orifice screen, and further comprising surrounding the particle impact and trap assembly with an enclosure.

18. The method of claim 17, further comprising admitting air between the lamp and the jet orifice screen at one end of the enclosure, and flowing air out an axial outlet at an opposite end of the enclosure, further comprising connecting a fan to the axial outlet, and drawing air with the fan into the inlet, between the lamp and the jet orifice screen, through the jet orifice screen, along the particle impact and trap assembly, through the enclosure and out through the outlet.

19. The method of claim 13, further comprising collecting particles above about 2 $\mu$m in the particle traps.

20. The method of claim 19, further comprising flowing air and remaining suspended particles through an outlet to a filter for collecting the remaining particles in the air.

21. The method of claim 13, further comprising collecting particles above about 2.5 $\mu$m and above in the particle traps.

22. The method of claim 21, further comprising flowing air and anions suspended particles through an outlet to a filter for collecting the remaining particles in the air.

23. A particle microtrap screen process, comprising etching multiple, relatively small microjet orifices through a relatively thin plate and forming a multiple microjet screen with microjets arranged in a pattern, forming multiple, relatively large microtrap openings in the same pattern through plural, relatively thick microtrap plates, forming aligned large gas passages in an impact plate and in the plural thick microtrap plates between the microtrap openings, assembling the multiple microjet screen on a peripheral spacer and assembling the plural microtrap plates on the spacer with the openings and the passages aligned and assembling the impact plate on the microtrap plates with the passages aligned, flowing gas with particles suspended therein to the microjet screen, flowing the gas with the particles entrained therein through the multiple microjets, accelerating the gas and the entrained particles, impacting the particles on the impact plate and collecting the particles in the microparticle traps, slowing and flowing the gas from which the particles have been removed between the microtrap plates and the microjet screen, and flowing the gas through the passages and out through a gas outlet.

24. The method of claim 23, wherein the impacting and collecting of particles comprises impacting and collecting particles having sizes about equal to or greater than 2 μm in the microparticle traps, and wherein slowing and flowing gas comprises slowing and flowing gas from which particles having sizes about equal to or greater than 2μm have been removed.

25. The method of claim 23, wherein the impacting and collecting of particles comprises impacting and collecting particles having sizes about equal to or greater than 2.5 μm in the microparticle traps, and wherein slowing and flowing gas comprises slowing and flowing gas from which particles having sizes about equal to or greater than 2 μm have been removed.

26. Particle microtrap screen apparatus, comprising a multiple microjet screen having multiple microjet orifices etched through a screen plate in a predetermined pattern, a spacer ring, microtrap plates relatively thicker than the microjet screen and having microtrap openings formed therethrough aligned with the microjet orifices in the predetermined pattern and having gas flow passages, an impact plate having aligned gas flow passages, for flowing gas with suspended particles from an inlet to the microjet screen and accelerating the gas and entraining the particles in the gas through the microjet orifices, and impacting the particles on the impact plate, trapping the particles in the microtraps and flowing gas from which particles have been removed through the passages to an outlet.

27. The apparatus of claim 26, further comprising a filter holder and filter on the outlet, and wherein impacting and trapping comprises impacting and trapping particles having sizes equal to or greater than about 2 μm, and wherein the flowing comprises flowing gas with fine particles from which particles≧about 2 μm have been removed through the passages and into the filter, filtering from the gas and remaining particles≦about 2 μm in the filter before flowing gas through the outlet.

28. The apparatus of claim 26, further comprising a filter holder and filter on the outlet, and wherein impacting and trapping comprises impacting and trapping particles having sizes equal to or greater than about 2.5 μm, and wherein the flowing comprises flowing gas with fine particles from which particles≧about 2.5 μm have been removed through the passages and into the filter, filtering from the gas and remaining particles≦about 2.5 μm in the filter before flowing gas through the outlet.

29. Particle microtrap screen apparatus, comprising a relatively thin jet screen having jet orifices etched therethrough, a spacer ring, plural relatively thick particle trap plates having particle trap openings etched therethrough, and an impact plate assembled with the plural particle trap plates having etched particle trap openings for forming multiple, relatively deep particle traps leading to an impact plate, the particle trap plates and the impact plate having enlarged openings for flowing gas therethrough to an outlet.

30. The apparatus of claim 29, further comprising a filter connected to the outlet for collecting fine particles which have not been impacted on the impact plate and trapped in the particle traps.

31. The apparatus of claim 30, wherein the particle traps trap particles≧about 2 μm, and wherein the filter collects particles≦about 2 μm.

32. The apparatus of claim 30, wherein the particle traps trap particles>about 2.54 m, and wherein the filter collects particles<about 2.5 gm.

* * * * *